US00PP11319P

United States Patent [19]

May

[11] Patent Number: Plant 11,319

[45] Date of Patent: Mar. 28, 2000

[54] CHRYSANTHEMUM PLANT NAMED 'DARK SPLENDOR'

[76] Inventor: Earl T. May, May Floral Company, Inc., 2223 Falcon Ridge La., Los Osos, Calif. 93402

[21] Appl. No.: 09/163,300

[22] Filed: Sep. 30, 1998

[51] Int. Cl.[7] ..... A01H 5/00

[52] U.S. Cl. ..... Plt./286

[58] Field of Search ..... Plt./286, 297

*Primary Examiner*—Howard J. Locker

*Attorney, Agent, or Firm*—Burns, Doane, Swecker & Mathis, L.L.P.

[57] ABSTRACT

A new and distinct cultivar of Chrysanthemum plant named Dark Splendor is provided. The new cultivar was the result of a naturally occurring mutation of unknown causation and is characterized by the formation of attractive darker lavender ray florets which can be readily distinguished from the lighter lavender ray florets of the parent Splendor cultivar (U.S. Plant Pat. No. 5,225). Also, the new cultivar tends to be slightly more vigorous and upright than its 'Splendor' parent. The new cultivar is particularly well suited for growing as a pot mum.

2 Drawing Sheets

SUMMARY OF THE INVENTION

The present invention comprises a new and distinct cultivar of *Dendranthema morifolium* Ramat., and hereinafter is referred to by the 'Dark Splendor' cultivar name.

The new cultivar is a mutation of unknown causation which was discovered as a sectoral chimera on two branches of one stem and carefully preserved during the course of plant selection work which was conducted by me. The new cultivar was discovered among plants of 'Splendor' cultivar (U.S. Plant Pat. No. 5,225) being grown under my direct supervision at Los Osos, Calif., which formed blossoms having the characteristic light lavender ray floret coloration and a flat capitulum form of the daisy type.

More specifically, the selection was made on Mar. 5, 1994 from among plants of the 'Splendor' cultivar being grown in 6.5 inch pots in a pot mum production program. The subject plant possessed five stems in total. A single stem of this plant had two terminal flowers which were found to display an attractive atypical darker lavender coloration from the rest of the plant. The balance of the plant continued to exhibit the lighter lavender blossom coloration typical of the 'Splendor' cultivar. Had I not discovered and preserved this new cultivar it would have been lost to mankind.

On Mar. 10, 1994 all flowers were removed from the plant. Also, all stems were removed except for the stem that had been observed to form both dark and light lavender flowers. Branches also were removed from the remaining stem which formed the typical lighter lavender blossoms of the 'Splendor' cultivar. This left only a plant with one stem with two branches that had been observed to form the atypical darker lavender flowers. The resulting plant was next placed in long day treatment to develop new vegetative growth.

On May 1, 1994 several vegetative cuttings were taken. These cuttings were rooted by direct stick in 6.5 inch pots in accordance with the conventional Chrysanthemum propagaion technique. On May 19, 1994 the resulting plants were placed in short day treatment to force flowering. During the next two months the plants were subjected to standard industry pot mum production techniques including the use of B-9 growth retardant, constant feed fertilization, and regular insecticide and fungicide treatments. Also, the plants were disbudded to create larger terminal flowers. On Jul. 19, 1994 the plants were in full bloom.

It was found that the new Chrysanthemum cultivar exhibits characteristics substantially the same as the parent 'Splendor' cultivar (U.S. Plant Pat. No. 5,225) with the exception that:

(a) the ray florets are darker lavender, (b) slightly more virgor is exhibited, and (c) the growth habit is slightly more upright.

Under extremely hot and bright conditions the dark lavender coloration will lose some of its brillance and take on a duller cast as the lavender coloration tends to separate along fine lines in the ray florets. This separation commonly is indiscernible unless observed in detail at a very close distance and/or with magnification. During the cooler/lower light months the darker lavender coloration tends to be more uniform throughout the ray florets and consequently in more brilliant in appearance.

The asexual reproduction of the new cultivar by cuttings, as performed at Los Osos, Calif., has demonstrated over a period in excess of three years that the characteristics of the new cultivar as herein described are firmly fixed and are well retained through successive generations of asexual propagation.

The 'Dark Splendor' cultivar has not been observed under all possible environmental conditions to date. Accordingly, it is possible that the phenotype may vary somewhat with variations in the environment, such as temperature, light, day length, contact with pesticides and/or subjection to growth retardant treatments. To date under the controlled conditions described herein, the characteristics of 'Dark Splendor' cultivar, other than floral ray coloration, vigor and growth habit as indicated have in all instances been very similar to those of the parent 'Splendor' cultivar. This combination of characteristics is capable of well distinguishing the new 'Dark Splendor' cultivar from all other known Chrysanthemum cultivars. See CHART A for comparison of characteristics of the new 'Dark Splendor' cultivar with those of the 'Splendor' cultivar.

For instance, it was found that the new 'Dark Splendor' cultivar can be readily distinguished fromt the 'White Splendor' cultivar (U.S. Plant Pat. No. 7,654) in view of the very different blossom coloration.

BRIEF DESCRIPTION OF THE PHOTOGRAPHS

The accompanying photographs show as nearly true as it is reasonably possible to make the same in color illustrations of this character, typical specimens of the plant and blossoms of the new cultivar. The plants of the new variety were grown in a glass greenhouse at Los Osos, Calif., under standard growing conditions and the photographs were taken outdoors in full sunlight at 1:00 p.m. on Mar. 15, 1997.

FIG. 1—illustrates a typical specimen of the overall plant of the new cultivar while growing in a 6.5 inch pot wherein the darker lavender ray florets of the blossoms is apparent.

FIG. 2—illustrates a closer view of typical blossoms of the new cultivar.

FIG. 3—illustrates for comparative purposes the darker lavender blossoms of the new 'Dark Splendor' cultiver at the lower right, the distinctive blossom coloration of the 'Cherry Splendor' cultivar at the lower left, and the lighter lavender blossoms of the 'Splendor' cultivar (U.S. Plant Pat. No. 5,225) at the top. The 'Cherry Splendor' cultivar is a mutation of the 'Dark Splendor' cultivar that was discovered by me which has not been previously released to the public.

DETAILED DESCRIPTION

Figure 1:
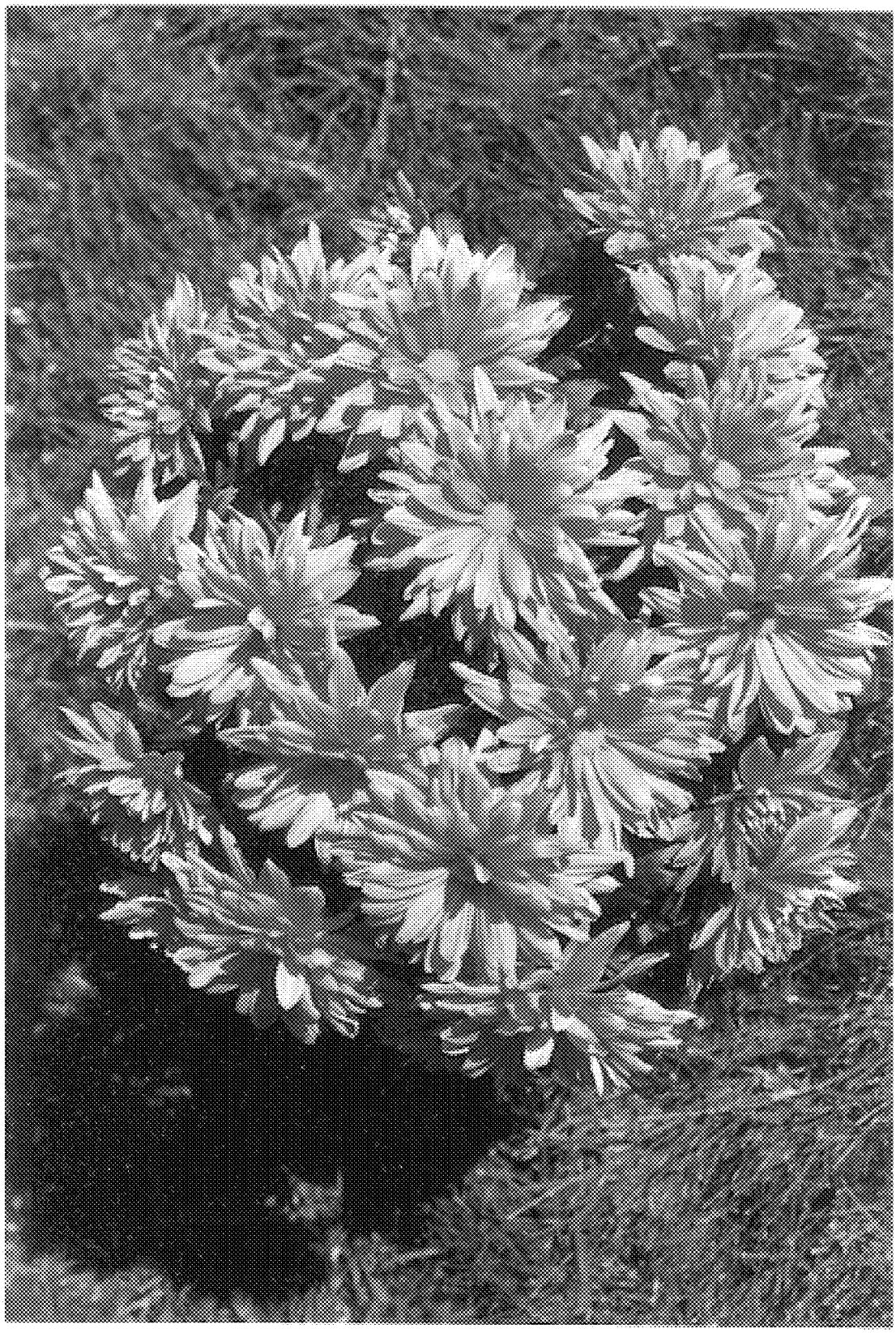
Figure 2:
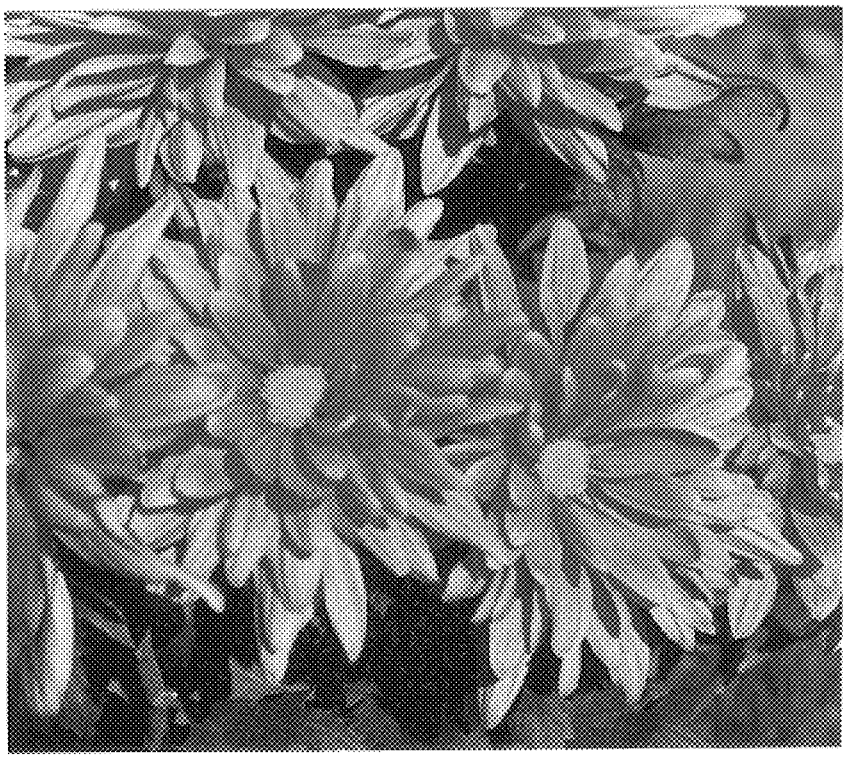
Figure 3:
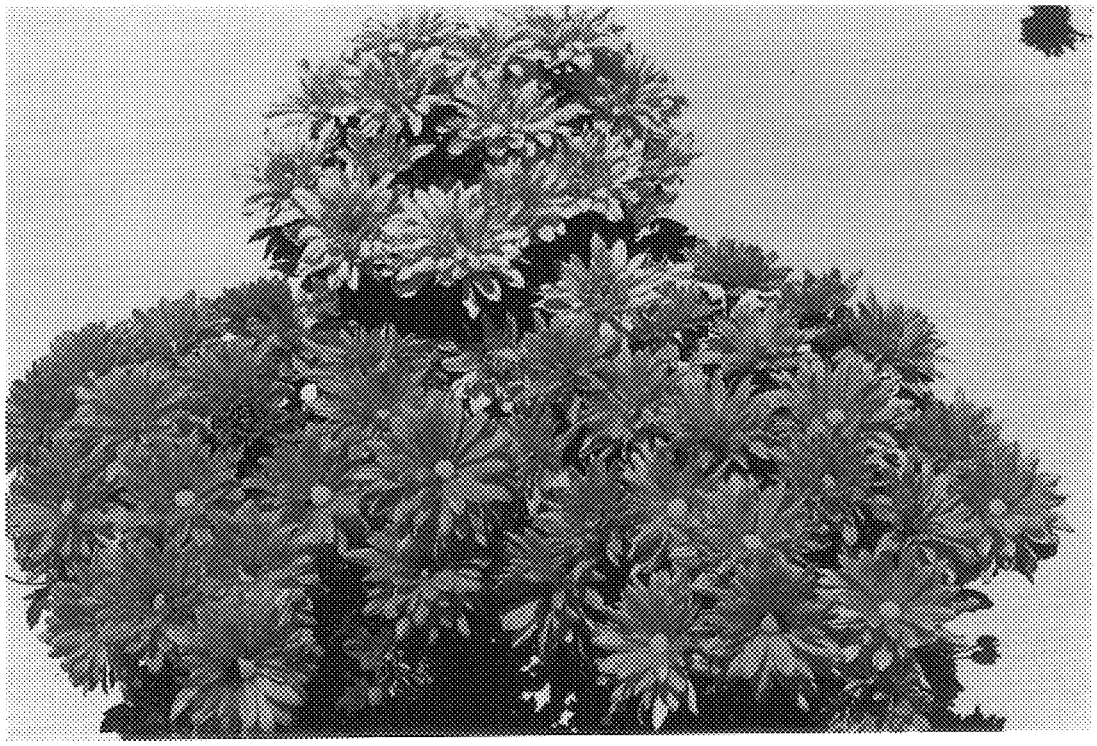

The chart used in the identification of colors described hereafter is The R.H.S. Colour Chart of The Royal Horticultural Society, London. The color values were determined on Mar. 15, 1997 between 12 noon and 1:00 p.m. under natural direct sunlight at Los Osos, Calif. The plants had been grown in 6.5 inch pots in a glass greenhouse under standard growing conditions. The glass greenhouse provided a very bright environment of high light intensity. Had the plants been grown under polyethylene the light encountered would have been more dispersed.

Classification:

*Botanical.*—*Dendranthema morifolium* Ramat., cv. 'Dark Splendor'.

*Commercial.*—Pot mum.

Inflorescence

A. Capitulum:

*Form.*—Flat.

*Type.*—Daisy or single.

*Diameter across face.*—Approximately 12 cm. on average.

B. Corolla of ray florets:

*Color* (*General tonality from a from a distance of one meter*).—Purple-lavender with a yellow center.

*Color* (*upper surface*).—Red-Purple Group 70A when subjected to normal growing temperatures, and when subjected to high light and temperature conditions Red-Purple Group 70A at the floret base closest to the disc florets fading to Red-Purple Group 70B in the middle and Red-Purple Group 70C at the tip.

*Color* (*lower surface*).—Red-Purple Group 74D.

C. Corolla of disc florets:

*Color* (*immature*).—Yellow-Green Group 151B.

*Color* (*mature*).—Yellow Group 12A.

D. Reproductive organs:

*Androecium.*—stamens are included in the corolla of the disc florets and pollen production is insignificant.

*Gynoecium.*—superior, one-celled and basal.

Plant

A. General appearance:

*Height.*—commonly varies between approximately 7 to 30 cm. above the edge of the pot depending on the size of the pot and the growing conditions. The smaller heights commonly are associated with the use of smaller pot sizes. The specified height was obtained with the use of B-9 growth retardant. Typical plant heights for untreated plants are not available.

Foliage:

*Color* (*upper surface*).—Yellow-Green Group 147A.

*Color* (*lower surface*).—Green Group 137B.

*Shape.*—ovate with a cuneate base.

*Margin.*—moderately lobed and pinnately parted and crenate with an obtuse tip.

CHART A

COMPARISON OF TYPICAL CHARACTERISTICS OF FINISHED PLANTS

| | 'Dark Splendor' | 'Splendor' |
|---|---|---|
| Diameter of Capitulum: | 12 to 13 cm. | 12 to 13 cm. |
| Diameter of Disc. | 1.8 cm. | 1.8 cm. |
| Thickness of Disc. | 1.2 cm. | 1.2 cm. |
| Average Number of Ray Florets | 65 | 75 |
| Length of Ray Corolla | 5.5 cm. | 5.6 cm. |
| Width of Ray Corolla | 1.4 cm. | 1.4 cm. |
| Color of Ray Corolla (front) | Red-Purple Group 70A with some fading to Red-Purple Group 70C to 70D | Purple Group 75C |
| Color of Ray Corolla (back) | Red-Purple Group 74D | Purple Group 75C |
| Length of Disc Corolla | 0.7 cm. | 0.7 cm. |
| Color Disc Corolla (immature) | Yellow-Green Group 151B | Yellow-Green Group 151B |
| Color Disc Corolla (mature) | Yellow Group 12A | Yellow Group 9A |
| Number of Flowers Per Stem. | Approximately 4 to 5 | Approximately 4 to 5 |
| Color of Foliage (front) | Yellow-Green Group 147A | Yellow-Green Group 147A |
| Color of Foliage (back) | Green Group 137B | Green Group 137B |
| Length of Largest Leaf | 15 cm. | 13.5 cm. |
| Width of Largest Leaf | 9 cm. | 8.5 cm. |
| Flowering Response Period | 9 weeks | 9 weeks |
| Growth Habit | Medium-tall | Medium |

I claim:

1. A new and distinct cultivar of Chrysanthemum plant that exhibits characteristics substantially the same as the parent 'Splendor' cultivar (U.S. Plant Pat. No. 5,225) with the exception that:

(a) the ray florets are darker lavender,
(b) slightly more vigor is exhibited, and
(c) the growth habit slightly more upright;

substantially as illustrated and described.

* * * * *